(12) United States Patent
Baileykobayashi et al.

(10) Patent No.: US 11,814,448 B2
(45) Date of Patent: Nov. 14, 2023

(54) CARRIER PEPTIDE FRAGMENT AND USE THEREOF

(71) Applicant: TOAGOSEI CO., LTD., Tokyo (JP)

(72) Inventors: Nahoko Baileykobayashi, Tsukuba (JP); Tetsuhiko Yoshida, Tsukuba (JP)

(73) Assignee: TOAGOSEI CO., LTD., Tokyo (JP)

( * ) Notice: Subject to any disclaimer, the term of this patent is extended or adjusted under 35 U.S.C. 154(b) by 49 days.

(21) Appl. No.: 17/525,097

(22) Filed: Nov. 12, 2021

(65) Prior Publication Data
US 2022/0153784 A1     May 19, 2022

(30) Foreign Application Priority Data

Nov. 17, 2020   (JP) .................................. 2020-190728

(51) Int. Cl.
*C07K 7/08*     (2006.01)
*C07K 14/00*     (2006.01)
*C12N 5/09*     (2010.01)

(52) U.S. Cl.
CPC ................ *C07K 7/08* (2013.01); *C07K 14/00* (2013.01); *C12N 5/0693* (2013.01); *C07K 2319/00* (2013.01)

(58) Field of Classification Search
None
See application file for complete search history.

(56) References Cited

U.S. PATENT DOCUMENTS

2012/0122210 A1    5/2012   Yoshida et al.

FOREIGN PATENT DOCUMENTS

JP     2005330206 A    12/2005
WO     2011013700 A1    2/2011

OTHER PUBLICATIONS

Spicer et al., "Peptide adn protein nanoparticle conjugates: versatile platforms for biomedical applications", Chem. Soc. Rev. 47: 3574-3620 (Year: 2018).*
Goyal P, Pandey D, Siess W. Phosphorylation-dependent regulation of unique nuclear and nucleolar localization signals of LIM kinase 2 in endothelial cells. J Biol Chem. Sep. 1, 2006;281(35):25223-30. doi: 10.1074/jbc.M603399200. Epub Jul. 4, 2006. PMID: 16820362.

* cited by examiner

*Primary Examiner* — Anand U Desai
(74) *Attorney, Agent, or Firm* — Young Basile Hanlon & MacFarlane, P.C.

(57) ABSTRACT

The present disclosure provides an artificially synthesized peptide fragment that can efficiently introduce a foreign substance of interest from outside a eukaryotic cell into at least the cytoplasm of the cell. The present disclosure also provides a method for using the peptide fragment. The herein disclosed peptide fragment is a peptide fragment for introducing a foreign substance of interest from outside a eukaryotic cell into at least the cytoplasm of the cell, and is provided with a repeat sequence in which the VVRSLVK amino acid sequence (SEQ ID NO: 1) is repeated at least two or more times. By using a construct that has the peptide fragment and the foreign substance of interest bonded to the N-terminal side and/or C-terminal side of the peptide fragment, the foreign substance of interest can be efficiently introduced from outside a eukaryotic cell into at least the cytoplasm of the cell.

6 Claims, 1 Drawing Sheet
Specification includes a Sequence Listing.

CARRIER PEPTIDE FRAGMENT AND USE THEREOF

CROSS-REFERENCE TO RELATED APPLICATIONS

This application claims priority to Japanese Patent Application No. 2020-190728 filed on Nov. 17, 2020, the contents of which are incorporated in this Specification in their entirety by reference.

REFERENCE TO SEQUENCE LISTING SUBMITTED VIA EFS-WEB

This application includes an electronically submitted sequence listing in .txt format. The .txt file contains a sequence listing entitled "TOAGOSEI CO., LTD." created on Sep. 14, 2021 and is 1,113 bytes in size. The sequence listing contained in this .txt file is part of the specification and is hereby incorporated by reference herein in its entirety.

TECHNICAL FIELD

The present disclosure relates to a method for introducing (transporting) a foreign substance from outside a eukaryotic cell into the interior of the cell, and to a carrier peptide fragment used in this method.

BACKGROUND

Foreign substances and particularly bioactive substances, e.g., polypeptides, have been introduced into the cells (eukaryotic cells) of, e.g., humans and other mammals, in order to change the characteristics of the cells (as well as tissues and organs composed of the cells) and/or to enhance or improve the function of the cells.

For example, WO 2011/013700 discloses a foreign substance introduction construct that contains a foreign substance of interest and the amino acid sequence described in SEQ ID NO: 2, which is described in Journal of Biological Chemistry, volume 281, number 35 (2006), pp. 25223-25230 and is known as the nucleolar localization signal (also abbreviated as "NoLS" in the following) of LIM kinase 2. LIM kinase 2 is a type of protein kinase that is present in human endothelial cells and participates in intracellular signaling. Because this amino acid sequence is an excellent cell membrane-penetrating peptide, this construct can very efficiently traverse the cell membrane of eukaryotic cells. This makes it possible to efficiently introduce the foreign substance of interest from outside a eukaryotic cell into the cytoplasm of the cell.

SUMMARY

There has been ever increasing interest in recent years in peptides that exhibit an excellent cell penetrating capability, and from, inter alia, a therapeutic perspective, there is desire for the development of art for the introduction of foreign substances into target cells at better efficiencies than heretofore available.

In order to respond to this desire, an object of the present disclosure is to provide a peptide fragment that can efficiently introduce a foreign substance of interest from outside a eukaryotic cell into at least the cytoplasm of the cell. A further object is to provide a foreign substance introduction construct that is constructed of said peptide fragment and the foreign substance. Yet another object is to provide a method that can efficiently introduce said construct from the outside of a eukaryotic cell into at least the cytoplasm of the cell.

In order to realize these objects, the present inventors sought an amino acid sequence that could be advantageously used as a peptide fragment (carrier peptide fragment) that would have an excellent cell membrane permeability and could introduce a foreign substance from the outside (i.e., outside the cell membrane) of a eukaryotic cell (particularly cell wall-free cells from various animals as represented by humans and other mammals) into at least the cytoplasm of the cell. The present inventors therefore focused on a partial amino acid sequence (VHL-related peptide motif), which is given by SEQ ID NO: 3, composed of 15 consecutive amino acid residues from position 157 to position 171 of the amino acid sequence of Von Hippel-Lindau (VHL) protein. This VHL-related peptide motif is an amino acid sequence discovered by the present inventors to be a peptide motif that participates in the induction of neural differentiation. In addition, the present inventors discovered that, when a repeat sequence is created in which the seven amino acid residues on the C-terminal side of this VHL-related peptide motif are repeated by artificial synthesis a plurality of times (at least two or more), the resulting sequence exhibits an excellent cell membrane permeability, thereby achieving the art of the present disclosure.

That is, the herein disclosed peptide fragment is a peptide fragment for introducing a foreign substance of interest from outside a eukaryotic cell into at least the cytoplasm of the cell, and is provided with a repeat sequence in which the following amino acid sequence:

```
                                          (SEQ ID NO: 1)
VVRSLVK
``` is repeated at least two or more times.

A peptide fragment with this construction exhibits an excellent cell membrane permeability.

In a preferred aspect of the herein disclosed peptide fragment, the boundary region between amino acid sequences given by SEQ ID NO: 1 in the repeat sequence either does not contain an additional amino acid residue or contains from 1 to 3 additional amino acid residues In this construction, the amino acid sequences given by SEQ ID NO: 1 are close to one another and an even better cell membrane permeability can be exhibited.

In another preferred aspect of the herein disclosed peptide fragment, the repeat sequence is provided with two of the amino acid sequences given by SEQ ID NO: 1.

With this construction, an excellent cell membrane permeability can be exhibited by a shorter sequence.

In order to realize the objects indicated above, this disclosure also provides an artificially constructed foreign substance introduction construct for introducing (transporting) a foreign substance of interest from the outside of a eukaryotic cell into at least the cytoplasm of the cell.

That is, the herein disclosed foreign substance introduction construct has a carrier peptide fragment comprising the herein disclosed peptide fragment, and has the foreign substance of interest bonded to the N-terminal side and/or the C-terminal side of the carrier peptide fragment.

This construction makes it possible to efficiently introduce the foreign substance of interest into a eukaryotic cell of interest.

This "foreign substance" refers to an inorganic compound or organic compound that can be directly bonded, or indirectly bonded through a suitable linker, to the N-terminal side or C-terminal side of the carrier peptide fragment, and that has a molecular size and chemical properties that support introduction into eukaryotic cells.

In a preferred aspect of the herein disclosed foreign substance introduction construct, the foreign substance is any organic compound selected from the group consisting of polypeptides, nucleic acids, dyes, and drugs.

Here, "polypeptide" refers to a polymer having a structure in which a plurality of amino acids are bonded by the peptide bond. There are no limitations on the number of peptide bonds (that is, the number of amino acid residues) in the polypeptide. Thus, polypeptides encompass both compounds generally known as peptides, which have approximately from 10 to fewer than 300 amino acid residues, and compounds generally known as proteins (typically macromolecular compounds composed of at least 300 amino acid residues). Polypeptides are not rigorously distinguished from proteins in this field. In this Specification, polypeptide is used to comprehensively refer to polymers composed of a plurality of amino acid residues (including oligomers).

In addition, "nucleic acid" refers to nucleotide polymers and includes DNA and RNA. This "nucleic acid" is not limited with respect to the number of bases.

Preferably the foreign substance is a mature polypeptide, or a precursor polypeptide thereof, derived from any species of organism, and the foreign substance introduction construct is a synthetic polypeptide having the amino acid sequence of the carrier peptide fragment and having an amino acid sequence that corresponds to a mature polypeptide, or precursor polypeptide thereof, serving as the foreign substance.

More preferably the amino acid sequence that corresponds to a mature polypeptide, or precursor polypeptide thereof, serving as the foreign substance is located at the N-terminal side of the carrier peptide fragment.

In order to realize the aforementioned objects, the present disclosure further provides a method for efficiently introducing (transporting) a foreign substance of interest from outside a eukaryotic cell into at least the cytoplasm of the cell. Thus, the herein disclosed foreign substance introduction method includes (1) a step of preparing the herein disclosed foreign substance introduction construct; (2) a step of supplying the foreign substance introduction construct to a sample that contains eukaryotic cells of interest; and (3) a step of incubating the sample to which the foreign substance introduction construct has been supplied, in order to introduce the construct into the eukaryotic cells in the sample.

The foreign substance introduction method with the above-described constitution can very efficiently introduce a foreign substance of interest into the cytoplasm by bringing about its passage across the cell membrane from outside a eukaryotic cell (outside of the cell membrane). The foreign substance introduction method achieves this by supplying (i.e., adding to living eukaryotic cells)—to a sample that contains eukaryotic cells of interest (for example, a culture containing the cells)—the foreign substance introduction construct that has been constructed by bonding, directly or indirectly via a suitable linker, the foreign substance of interest (typically an organic compound such as, for example, a polypeptide, nucleic acid, dye, or drug) to the N-terminal side and/or C-terminal side of the carrier peptide fragment.

In a preferred aspect of the herein disclosed foreign substance introduction method, the foreign substance is characteristically any organic compound selected from the group consisting of polypeptides, nucleic acids, dyes, and drugs. A construct fabricated so as to contain organic compounds of this type can be efficiently introduced into cells of interest.

In another preferred aspect of the herein disclosed foreign substance introduction method, the foreign substance is a mature polypeptide, or a precursor polypeptide thereof, derived from any species of organism, and the foreign substance introduction construct is a synthetic polypeptide that has the amino acid sequence of the carrier peptide fragment and that has, as the foreign substance, an amino acid sequence corresponding to the mature polypeptide or a precursor polypeptide thereof.

This construction makes it possible to efficiently introduce the mature polypeptide, or a precursor polypeptide therefore, into eukaryotic cells of interest.

In yet another preferred aspect of the herein disclosed foreign substance introduction method, the amino acid sequence corresponding to the mature polypeptide, or a precursor polypeptide thereof, is located as the foreign substance at the N-terminal side of the carrier peptide fragment.

This construction makes it possible to even more efficiently introduce the mature polypeptide or precursor polypeptide thereof into eukaryotic cells of interest.

In still another preferred aspect of the herein disclosed foreign substance introduction method, the eukaryotic cells that are the target for the introduction of the foreign substance introduction construct are human or nonhuman mammalian cells.

This construction makes it possible to efficiently introduce the foreign substance into the cytoplasm of human or nonhuman mammalian cells.

DETAILED DESCRIPTION

Preferred embodiments of the herein disclosed art are described in the following. Matters required for implementation but not particularly described in this Specification (for example, general matters related to methods for the chemical synthesis of peptides, cell culture techniques, and the preparation of compositions that contain peptides and/or nucleic acids as components) can be understood as design matters for the individual skilled in the art based on the conventional art in fields such as cell engineering, physiology, medicine, pharmaceutical science, organic chemistry, biochemistry, genetic engineering, protein engineering, molecular biology, genetics, and so forth.

The herein disclosed art can be implemented based on the contents disclosed in this Specification and the common general technical knowledge in the pertinent fields. In the description that follows, the amino acids are represented, depending on the circumstances, by the single letter codes (except that three letter codes are used in the sequence listings) stipulated by the nomenclature for amino acids given in the IUPAC-IUB guidelines. Unless specifically indicated otherwise, in this Specification "amino acid residue" is a term that encompasses the N-terminal amino acid and the C-terminal amino acid of the peptide chain.

In this Specification, "synthetic peptide" refers to a peptide fragment for which the peptide chain thereof does not exist by itself in an independent and stable manner in nature, but rather is produced by artificial chemical synthesis or biosynthesis (i.e., production based on genetic engineering) and can exist in a stable manner in a prescribed composition. Herein, "peptide" is a term that indicates an amino acid polymer having a plurality of peptide bonds, and there is no limitation with regard to the number of amino acid residues.

For the amino acid sequences described in this Specification, the left side is always the N-terminal side and the right side always indicates the C-terminal side. When a numerical value range is described in this Specification using "A to B" (A and B are any numerical values), this carries the usual interpretation and means from at least A to not more than B.

The herein disclosed peptide fragment is provided with a repeat sequence in which VVRSLVK (SEQ ID NO: 1) is repeated at least two or more times.

This "repeat sequence" denotes an amino acid sequence in which the amino acid sequence given by SEQ ID NO: 1 is repeated two or more times (for example, 2, 3, 4, or 5 or more times). In other words, designating the amino acid sequence composed of the 7 amino acid residues given by SEQ ID NO: 1 as 1 unit, the "repeat sequence" refers to an amino acid sequence provided with at least 2 or more units (for example, 2 units, 3 units, 4 units, or 5 or more units).

The amino acid sequence with SEQ ID NO: 1 is an amino acid sequence composed of the total of 7 amino acid residues from position 165 to position 171 from the N-terminal of the amino acid sequence of the Von Hippel-Lindau (VHL) protein, which is known to be expressed in neurons of the central nervous system. The amino acid sequence with SEQ ID NO: 1 is composed of the 7 amino acid residues on the C-terminal side of the amino acid sequence, given by SEQ ID NO: 3, composed of the total of 15 amino acid residues from position 157 to position 171 from the N-terminal of VHL protein. As reported in Japanese Patent Application Publication No. 2005-330206, the amino acid sequence given by SEQ ID NO: 3 is known as a VHL-related peptide motif and is known to exhibit the ability to induce neuron differentiation.

Typically additional amino acid residues are not present at between (boundary region) the amino acid sequences with SEQ ID NO: 1 and the amino acid sequences with SEQ ID NO: 1 are directly bonded to each other consecutively. However, within a range in which the cell membrane permeability is not impaired, these amino acid sequences may be indirectly bonded to each other across a linker; for example, a peptide linker composed of additional amino acid residues may be provided. The peptide linker can contain, for example, from 1 to 10 (typically from 1 to 3) additional amino acid residues. The additional amino acid residues are not particularly limited, but are preferably, for example, amino acids that have small side chains and do not have an effect on the charge. For example, the presence is preferred of one or two or more amino acid residues selected from, e.g., glycine, alanine, and serine.

The herein disclosed peptide fragment typically exhibits an amino acid sequence provided with a repeat sequence in which the amino acid sequence given by SEQ ID NO: 1 is repeated at least two or more times, but, insofar as the cell membrane permeability is not impaired, it encompasses sequences provided by modification of the amino acid sequence with SEQ ID NO: 1. These "modified sequences" are amino acid sequences (modified amino acid sequences) formed by the substitution, deletion, and/or addition (insertion) of one amino acid residue or a plurality (typically 2 or 3) of amino acid residues. Such slightly modified sequences can be readily used by the individual skilled in the art based on the herein disclosed information and as a consequence are encompassed by the "peptide fragment (carrier peptide fragment)" as a herein disclosed technical concept.

The following, for example, are typical examples of modified sequences in this Specification: sequences produced by so-called conservative amino acid replacement in which 1, 2, or 3 amino acid residues are conservatively replaced, and sequences provided by the addition (insertion) or deletion of 1, 2, or 3 amino acid residues to/from the prescribed amino acid sequence. Typical examples of conservative substitutions are, for example, sequences in which a basic amino acid residue is substituted by a different basic amino acid residue (for example, exchange between a lysine residue and arginine residue), and sequences in which a hydrophobic amino acid residue is substituted by a different hydrophobic amino acid residue (for example, exchange among the leucine residue, isoleucine residue, and valine residue).

The herein disclosed peptide fragment is typically an amino acid sequence composed of the aforementioned repeat sequence wherein the N-terminal and C-terminal of this peptide fragment are the amino acid sequence given by SEQ ID NO: 1. However, within a range in which the cell permeability is not lost, other amino acid residues may be present at the N-terminal side and C-terminal side. For example, 1 or a plurality (typically 2 or 3) of other amino acid residues may be present at the N-terminal side and C-terminal side.

The amino acid sequence given by SEQ ID NO: 4 is an amino acid sequence composed of a total of 14 amino acid residues, in which two of the amino acid sequences given by SEQ ID NO: 1 are consecutively bonded; this is an example of a typical amino acid sequence of the herein disclosed carrier peptide fragment. An excellent cell membrane permeability is exhibited by amino acid sequences composed of a repeat sequence in which the amino acid sequence given by SEQ ID NO: 1 is repeated two or more times, such as the amino acid sequence given by SEQ ID NO: 4.

The herein disclosed foreign substance introduction construct has a carrier peptide fragment composed of the herein disclosed peptide fragment and has the foreign substance of interest bonded to the N-terminal side and/or C-terminal side of this carrier peptide fragment.

The herein disclosed "carrier peptide fragment" is a sequence defined (comprehended) by the amino acid sequence of the herein disclosed peptide fragment, and is an amino acid sequence that exhibits cell membrane permeability for eukaryotic cells. As a consequence, the foreign substance introduction construct having this carrier peptide fragment and a foreign substance of interest bonded to the N-terminal side and/or C-terminal side of this carrier peptide fragment, is introduced at high efficiencies from the outside of a eukaryotic cell into at least the cytoplasm of the cell.

The foreign substance introduction construct can be designed and constructed by bonding (connecting) a desired foreign substance, either directly or indirectly via an appropriate linker, to the N-terminal side and/or C-terminal side of the aforementioned carrier fragment.

There are no particular limitations on the linker, and it may be a peptide linker or a nonpeptide linker. While this does not constitute a particular limitation, the amino acid sequence constituting a peptide linker preferably is an amino acid sequence that does not produce steric hindrance and is flexible. The peptide linker can be, for example, a linker that contains one or two or more species of amino acid residues selected from glycine, alanine, serine, and so forth and that is composed of not more than 10 amino acid residues (more preferably from 1 to 5, for example, 1, 2, 3, 4, or 5 amino acid residues). This linker may use β-alanine. While this does not constitute a particular limitation, for example, an alkyl linker, polyethylene glycol (PEG) linker, aminohexanoyl spacer, and so forth may be used for the nonpeptide linker.

The foreign substance is typically an organic compound such as a polypeptide, nucleic acid, dye, or drug.

The foreign substance can be, for example, a polypeptide. When the foreign substance is a polypeptide, the foreign substance introduction construct of interest can be fabricated by designing a peptide chain that contains the amino acid sequence constituting this polypeptide and the amino acid sequence constituting the carrier peptide fragment, and by carrying out the biosynthesis or chemical synthesis of this peptide chain. In addition, foreign substance introduction constructs can be constructed by the direct or indirect bonding, using various heretofore known chemical methods, of a nucleic acid, e.g., various DNAs and RNAs, a dye (for example, various fluorescent dye compounds, e.g., FAM, FITC), or an organic compound that functions as a drug (for example, antitumor agents, including nucleic acid-type antitumor agents, e.g., 5-fluorouracil (5FU), antivirals such as azidothymidine (AZT)) to the N-terminal side and/or C-terminal side of the hereinabove-described carrier peptide fragment.

While this is not a particular limitation, the function possessed by the foreign substance can be, for example, promotion of the induction of differentiation of stem cells (stem cell differentiation induction activity), inhibition of the proliferation of tumor cells (antitumor activity), inhibition of the proliferation of virus-infected cells (antiviral activity), and so forth.

There are no particular limitations on the number of foreign substances bonded to the carrier peptide fragment in the foreign substance introduction construct. Thus, one or two or more foreign substances may be bonded to one carrier peptide fragment. While this is not a particular limitation, for example, a polypeptide, nucleic acid, drug, etc., may be bonded to the N-terminal side of one carrier peptide fragment and a dye may be bonded to the C-terminal side thereof. The bonding of a dye to the carrier peptide fragment facilitates evaluation of the efficiency of introduction into the eukaryotic cell of the foreign substance introduction construct and evaluation of the localization within the cell, and is thus preferred.

When the foreign substance is a polypeptide, there are no particular limitations on the polypeptide (amino acid sequence) that may be used. For example, a polypeptide may be used that has a relatively large number of amino acid residues, such as a polypeptide or protein that has approximately 100 to 1,000 amino acid residues.

The total number of amino acid resides comprising the synthetic peptide that is fabricated as the foreign substance introduction construct is typically at least several to several tens (for example, 10), and is suitably not more than 1,000, preferably not more 600, still more preferably not more than 500, and particularly preferably not more than 300 (for example, 10 to 300). Polypeptides of this length are easy to synthesize (biosynthesis, chemical synthesis) and easy to use.

The foreign substance is preferably the mature form of, or a precursor for (including proforms and pre-proforms), a polypeptide involved in a function such as the development, differentiation, growth, malignant transformation, homeostasis, regulation of metabolism, and so forth of various cells and tissues (organs). In addition, through the introduction into a cell of a polypeptide for which the function is not yet known, the herein disclosed foreign substance introduction method can also be used to elucidate the function within a cell (within biological tissue) of the polypeptide.

For example, when the eukaryotic cell that is the target of foreign substance introduction is a human or other mammalian stem cell, it will be advantageous to use the mature form of, or a precursor for, a polypeptide having any of various biological activities involved with the induction of stem cell differentiation. Here, "stem cell" encompasses somatic stem cells, embryonic stem cells, and induced pluripotent stem cells (iPS stem cells). When the eukaryotic cell that is the target of foreign substance introduction is a cancer cell (tumor cell), it will be advantageous to use various polypeptides involved in the induction of apoptosis of the cancer cells (tumor cells). Or, in this case it will be advantageous to use a polypeptide that can prevent cancer cells (tumor cells) from suppressing the function of the immune surveillance system. When the eukaryotic cell that is the target of introduction is a bacterially infected cell or a virally infected cell, it will be advantageous to use various polypeptides involved with the induction of apoptosis of the infected cells, and/or polypeptides that can inhibit the growth of the bacteria or virus in the infected cells, and/or polypeptides that an inhibit an increase in bacterial or viral infection from the infected cells.

Just as for the carrier peptide fragment, the polypeptide serving as the foreign substance may include, insofar as its function is preserved, a modified amino acid sequence formed by the substitution, deletion, and/or addition (insertion) of one or several amino acid residues.

The foreign substance introduction construct is preferably a foreign substance introduction construct in which at least one amino acid residue has been converted to the amide. The structural stability (for example, protease resistance) of the foreign substance introduction construct in the cytoplasm and nucleus can be improved when the carboxyl group of the amino acid residues (typically the C-terminal amino acid residue of the peptide chain) is converted to the amide.

For example, when the foreign substance is bonded to the N-terminal side of the carrier peptide fragment, the C-terminal amino acid residue of the carrier peptide fragment is preferably converted to the amide. In addition, when, for example, the foreign substance is a polypeptide and this polypeptide is bonded to the C-terminal side of the carrier peptide fragment, the C-terminal amino acid residue of the polypeptide is preferably converted to the amide.

A herein disclosed peptide fragment or foreign substance introduction construct with a relatively short peptide chain (including the polypeptide constituting the foreign substance, the carrier peptide fragment, and the peptide linker) can be readily produced based on general chemical synthesis methods. For example, a heretofore known solid-phase synthesis method or liquid-phase synthesis method may be used. A solid-phase synthesis method using Boc (t-butyloxycarbonyl) or Fmoc (9-fluorenylmethoxycarbonyl) as the amino group protection group is preferred. Thus, the aforementioned peptide chain having the desired amino acid sequence and modified moieties (e.g., C-terminal amidation) can be synthesized by solid-phase synthesis using a commercial peptide synthesizer. For example, only a portion of the peptide chain may be synthesized by this method, for example, only the carrier peptide fragment, or a peptide chain containing the carrier peptide fragment and a peptide linker moiety may be synthesized by this method.

Alternatively, production may be carried out by biosynthesis of the peptide moiety based on genetic engineering methods. Thus, a polynucleotide (typically DNA) having a nucleotide sequence (containing the ATG start codon) encoding the desired amino acid sequence is synthesized. A recombinant vector having a gene expression construct comprising the synthesized polynucleotide (DNA) and various control elements (including a promoter, ribosome binding site, terminator, enhancer, and various cis elements that control the expression level) for bringing about the expression of the amino acid sequence in a host cell is constructed in correspondence to the host cell.

Using ordinary methods, this recombinant vector is introduced into a prescribed host cell (for example, yeast, insect cells, plant cells), and the host cell, or tissue or a specimen containing these cells, is cultured under prescribed conditions. The target peptide can thereby be produced in the cells. The peptide moiety is isolated from the host cell (from the medium when it has been secreted), and the target peptide moiety can be obtained by carrying out refolding, purification, and so forth, as necessary.

With regard to the method for constructing the recombinant vector, the method for introducing the constructed recombinant vector into a host cell, and so forth, methods already being used in this field may be directly used, and their detailed description has been omitted since these methods as such are not a particular characteristic feature of the present disclosure.

For example, a fusion protein expression system can be used in order to bring about the efficient production of large amounts in a host cell. Thus, a gene (DNA) encoding the amino acid sequence of the target polypeptide is chemically synthesized, and the synthetic gene is introduced into the appropriate site in a suitable fusion protein expression vector (for example, the pET series available from Novagen, or a GST (glutathione S-transferase) fusion protein expression vector, such as the pGEX series available from Amersham Bioscience). A host cell (typically *E. coli*) is transformed with this vector. The resulting transformant is cultured to produce the target fusion protein. This protein is then extracted and purified. The obtained purified fusion protein is cleaved with a prescribed enzyme (protease), and the liberated target peptide fragment (i.e., the designed artificial polypeptide) is recovered by a method such as affinity chromatography. A desired foreign substance introduction construct (artificial polypeptide) can be produced using such a heretofore known fusion protein expression system (for example, the GST/His system provided by Amersham Bioscience).

Alternatively, a target polypeptide can be synthesized in vitro using a so-called cell-free protein synthesis system, by constructing a template DNA (i.e., a synthetic gene fragment that contains a nucleotide sequence encoding the amino acid sequence of the peptide moiety of the foreign substance introduction construct) for use in the cell-free protein system and by using the various compounds (ATP, RNA polymerase, amino acids, and so forth) required for synthesis of the peptide moiety. For example, the reports by Shimizu et al. (Shimizu et al., Nature Biotechnology, 19, 751-755 (2001)) and Madin et al. (Madin et al., Proc. Natl. Acad. Sci. USA, 97(2), 559-564 (2000)) are references for cell-free protein synthesis systems. At the time of the filing of the instant patent application, numerous enterprises were already performing contract polypeptide production based on the technology described in these reports and cell-free protein synthesis kits based on the technology described in these reports were commercially available (for example, kits can be acquired from CellFree Sciences Co., Ltd. in Japan).

The single-stranded or double-stranded polynucleotide containing the nucleotide sequence encoding the peptide moiety of the foreign substance introduction construct, and/or containing the nucleotide sequence complementary to this sequence, can be readily produced (synthesized) using heretofore known methods. Thus, by selecting the codons corresponding to the individual amino acid residues comprising the designed amino acid sequence, the nucleotide sequence corresponding to this amino acid sequence can be readily determined and provided. Once the nucleotide sequence has been determined, the polynucleotide (single-stranded) corresponding to the desired nucleotide sequence can be readily obtained using, for example, a DNA synthesizer. Using the obtained single-stranded DNA as a template, the target double-stranded DNA can be obtained using various enzymatic synthesis means (typically PCR). The polynucleotide may be in the form of DNA or in the form of RNA (e.g., mRNA). The DNA can be provided as the double strand or single strand. When provided as the single strand, it may be the coding strand (sense strand) or may be the noncoding strand (antisense strand) having the complementary sequence thereto.

The thusly obtained polynucleotide can be used as material for constructing a recombinant gene (expression cassette) for peptide production in various host cells or using a cell-free protein synthesis system, as described in the preceding.

The foreign substance introduction construct can be favorably used as an effective component in compositions that are applied based on the function of the foreign substance. The foreign substance introduction construct may take the form of a salt insofar as the function of the foreign substance is not impaired. For example, use can be made of the acid-addition salt that can be obtained using a common method by the addition reaction of a commonly used inorganic acid or organic acid. The "foreign substance introduction construct" described in this Specification and in the claims thus encompasses these salt forms.

The foreign substance introduction construct can be provided in the form of a composition that can contain, in addition to the foreign substance introduction construct functioning as the effective component, any of various medically (pharmaceutically) acceptable carriers in accordance with the form of use.

A carrier as generally used in peptide drugs as, for example, a diluent, excipient, and so forth, is preferred for this carrier. This carrier can differ as appropriate in correspondence to the application and form of the foreign substance introduction construct, but is typically water, a physiological buffer solution, or any of various organic solvents. In addition, this carrier can be an aqueous solution of an alcohol (e.g., ethanol) at a suitable concentration, or can be glycerol or a nondrying oil such as olive oil, or may be a liposome. In addition, secondary components that can be incorporated in the drug composition can be exemplified by various fillers, expanders, binders, moisturizers, surfactants, dyes, fragrances, and so forth.

There are no particular limitations on the form of the composition. Typical forms can be exemplified by liquids, suspensions, emulsions, aerosols, foams, granules, powders, tablets, capsules, and ointments. In addition, for use as, inter alia, an injectable, a lyophilized material or granulated material can be made in order to support the preparation of a drug solution by dissolution in, for example, physiological saline or a suitable buffer solution (for example, PBS) immediately prior to use.

The processes as such for the preparation of various drug formulations (compositions) using the foreign substance introduction construct (main component) and various carriers (secondary components) as materials may be based on heretofore known methods, and a detailed description of these formulation methods as such is omitted because they are not a characteristic feature of the present disclosure. A source of detailed information with regard to formulations is, for example, Comprehensive Medicinal Chemistry, edited by Corwin Hansch, Pergamon Press (1990).

Also provided is a method, using the herein disclosed foreign substance introduction construct (composition), for introducing the foreign substance introduction construct within an organism (in vivo) or outside an organism (in vitro). In general terms, this method comprises the following steps (1) to (3):

(1) a step of preparing the herein disclosed foreign substance introduction construct;
(2) a step of supplying the foreign substance introduction construct to a sample that contains eukaryotic cells of interest; and
(3) a step of incubating the sample to which the foreign substance introduction construct has been supplied, in order to introduce the construct into the eukaryotic cells in the sample.

With regard to in vivo, the "eukaryotic cells" here encompass, for example, various tissues, viscera, organs, blood, and lymph. With regard to in vitro, the "eukaryotic cells" here encompass, for example, various cell aggregates, tissues, viscera, organs, blood, and lymph removed from an organism, as well as cell lines.

For in vivo, compositions containing the hereinabove disclosed construct can be used in accordance with the methods and use amounts that correspond to the form of the composition and the goals therefor. For example, precisely the desired amount can be administered as a liquid to a diseased region (for example, malignant tumor tissue, virally infected tissue, inflamed tissue) of a patient (i.e., an organism) by intravenous, intramuscular, subcutaneous, intradermal, or intraperitoneal injection. Alternatively, a solid form, e.g., a tablet, or a gel or aqueous jelly, e.g., an ointment, can be administered directly to a prescribed tissue (i.e., for example, a diseased region, e.g., a tissue or organ that contains, e.g., tumor cells, virally infected cells, inflamed cells). Alternatively, a solid form, e.g., a tablet, can be administered orally. In the case of oral administration, the use is preferred of an encapsulating or protective (coating) material in order to prevent degradation by digestive enzymes in the digestive tract.

Alternatively, for eukaryotic cells that are cultured outside an organism (in vitro), a suitable amount of the herein disclosed composition (i.e., a suitable amount of the foreign substance introduction construct) may be supplied at least once to the culture medium for the target eukaryotic cells. The amount per supply and number of times of supply are not particularly limited because they will vary with, for example, the species of eukaryotic cell being cultured, cell density (cell density at the start of culture), number of subcultures, culture conditions, and type of culture medium. For example, a single addition or a plurality of additions, i.e., twice or more, is preferably made so as to provide a carrier peptide fragment concentration in the culture medium within the range of approximately at least 0.05 µM and not more than 100 µM, for example, within the range of at least 0.5 µM and not more than 50 µM, and, for example, within the range of at least 1 µM and not more than 20 µM.

An example of an in vitro method of introduction is given in the examples below.

There are no particular limitations on methods for evaluating the efficiency of introduction of the foreign substance introduction construct. For example, when a dye (typically a fluorescent dye compound) is bonded to this construct, the efficiency of introduction into eukaryotic cells can be evaluated using microscopic observations (for example, fluorescence microscopic observations) or flow cytometry. The efficiency of construct introduction can also be evaluated by an immunochemical method (e.g., western blot or immune cell staining) that uses an antibody that specifically recognizes the peptide moiety of the construct.

Several examples relating to the herein disclosed art are described in the following, but this should not be construed as limiting the herein disclosed art to what is shown in these examples.

Fabrication of Foreign Substance Introduction Constructs

The two synthetic peptides (peptide 1 and peptide 2) shown in Table 1 were prepared. Peptide 1 is a peptide fragment (carrier peptide fragment) composed of the amino acid sequence given by SEQ ID NO: 4 and is a typical example of the herein disclosed peptide fragment. Peptide 2 is an amino acid sequence, given by SEQ ID NO: 2, known as a nucleolar localization signal (NoLS) of the LIM kinase 2 present in human endothelial cells, and is the carrier peptide fragment disclosed in WO 2011/013700.

Peptide 1 and peptide 2 were both synthesized by carrying out solid-phase synthesis (Fmoc method) using a commercial peptide synthesizer and following the manual provided therewith. In addition, both peptide 1 and peptide 2 were synthesized with the carboxyl group (—COOH) of the C-terminal amino acid residue being converted to the amide (—CONH$_2$).

The method as such for using the peptide synthesizer is not a characteristic feature of the present disclosure, and a detailed explanation thereof has therefore been omitted.

TABLE 1

| Peptide No. | Amino acid sequence | SEQ ID NO: |
|---|---|---|
| 1 | VVRSLVKVVRSLVK | 4 |
| 2 | KKRTLRKNDRKKR | 2 |

A foreign substance introduction construct provided with peptide 1 (also referred to as "sample 1") and a foreign substance introduction construct provided with peptide 2 (also referred to as "sample 2") were then prepared by directly bonding, based on a standard method, the fluorescent dye FAM ($C_{21}H_{12}O_7$: 5(6)-carboxyfluorescein, molecular weight=376.3, excitation wavelength=495 nm, fluorescence wavelength=520 nm) as the foreign material to the amino acid residue on the N-terminal side of peptide 1 and peptide 2, respectively. Sample 1 and sample 2 were each diluted with DMSO to prepare a sample solution 1 having a sample 1 concentration of 2 mM and a sample solution 2 having a sample 2 concentration of 2 mM.

Evaluation of the Cell Membrane Permeability of Sample 1 and Sample 2

The cell membrane permeability of sample 1 and sample 2 was evaluated using HeLa cells (an established cell line derived from human cervical cancer cells) as the eukaryotic cells. As shown in Table 2, Example 1 indicates a test in which the sample solution 1 was added to a HeLa cell culture medium; Example 2 indicates a test in which the sample solution 2 was added to a HeLa cell culture medium; and Example 3 indicates a test in which a DMSO-diluted FAM solution was added to a HeLa cell culture medium.

TABLE 2

|  | Addition |
|---|---|
| Example 1 | FAM-VVRSLVKVVRSLVK-CONH$_2$ |
| Example 2 | FAM-KKRTLRKNDRKKR-CONH$_2$ |
| Example 3 | FAM |

Example 1

HeLa cells were cultured on DMEM (Dulbecco's modified Eagle's medium (Cat. No. 043-30085, from FUJIFILM Wako Pure Chemical Corporation)) containing 10% FBS (fetal bovine serum), which is a general culture medium.

The HeLa cells attached to the culture plate were washed with PBS, a 0.25% trypsin/EDTA solution was then added, and incubation was carried out for 3 minutes at 37° C. After this incubation, the aforementioned DMEM containing 10% FBS was added and the trypsin was inactivated, and the cells were then sedimented by carrying out centrifugal separation for 5 minutes at 150×g. The supernatant produced by the centrifugal separation was removed, and the aforementioned DMEM containing 10% FBS was added to the sediment (cell pellet) to prepare a cell suspension containing approximately 1×10$^5$ cells/mL. The cells were seeded (approximately 2×10$^5$ cells/well) by the addition of 2 mL of this cell suspension to the wells of a commercial 6-well plate ((Iwaki microplate commercially available from AGC techno glass Co., Ltd). The cells were attached to the well bottom by culture for 3 hours at 37° C. under the condition of 5% CO$_2$.

The 2 mM sample solution 1 was then diluted with the aforementioned DMEM containing 10% FBS to prepare a sample solution 1 in which the sample 1 concentration was 20 μM. After the aforementioned 3-hour culture, 1 mL of the culture supernatant was removed from the wells, followed by the addition to the wells of 1 mL of the 20 μM sample solution 1 (i.e., the concentration of sample 1 in the culture medium in the wells was brought to 10 μM and the DMSO concentration was brought to 0.5%). The cells were incubated for 20 hours at 37° C. under the condition of 5% CO$_2$. After this 20-hour incubation, the culture supernatant was removed from the wells and the cells in the wells were washed twice with 1 mL PBS. 200 μL of 0.25% trypsin/EDTA was then added to the wells and incubation was carried out for 3 minutes at 37° C. After this incubation, the trypsin was inactivated by the addition of 400 μL of the aforementioned DMEM containing 10% FBS to the wells, and the cells were subsequently recovered by transferring the cell suspensions in the wells to a tube. The wells were then washed by the further addition of 600 μL PBS to the wells. The cells that had remained in the wells were recovered to the tube by transferring the PBS in the wells to the tube. Centrifugal separation was run on this tube for 5 minutes using conditions of 4° C. and 210×g. After the centrifugal separation, the supernatant was removed, the sediment (cell pellet) was suspended (washed) with 1 mL of PBS, and centrifugal separation was carried out using the same conditions as before. After this procedure has been repeated twice, the supernatant was removed to obtain cells (cell pellet) that had been cultured on a sample 1-containing culture medium.

The cell permeability of sample 1 was analyzed using the resulting cells (cell pellet) and a flow cytometer. An On-Chip Flow Cytometer (On-chip Biotechnologies Co., Ltd.) was used for the flow cytometer.

For this analysis, the cell pellet obtained as described above was suspended in 50 μL PBS. To this suspension was added 50 μL of 2×Sample Buffer for use with the indicated flow cytometer to prepare a cell suspension for submission to analysis.

Gating was performed using this flow cytometer based on forward scatter (FSC) and side scatter (SSC); the gating was set for the cell population that was the target of the analysis; and the fluorescent intensity was measured for the cell population within this gating. The analysis was performed so this cell population reached approximately 10,000. The FL2 fluorescence detector on the indicated flow cytometer, which could detect the fluorescence wavelength of FAM, was used to measure the fluorescent intensity. The measurement results were analyzed using "FlowJo (registered trademark)" (Tree Star Inc.) commercial analysis software to obtain the mean fluorescent intensity (MFI) for the cell population that was the measurement target.

Example 2

This was carried out as in Example 1, except that the sample solution 2 was used in place of the sample solution 1.

Example 3

This was carried out as in Example 1, but using the DMSO-diluted FAM solution in place of the sample solution 1. A FAM solution concentration was used that provided the same concentrations as the sample 1 solution (i.e., a concentration was used that brought the FAM concentration in the culture medium in the wells to 10 μM and the DMSO concentration to 0.5%).

Figure 1:
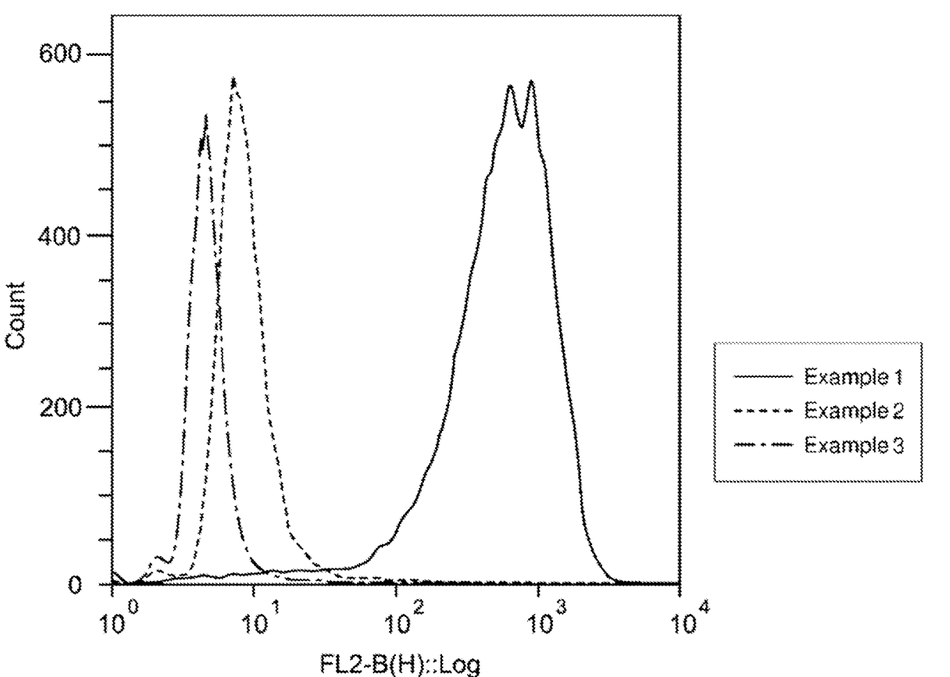
FIG. 1 is a histogram that shows the relationship between fluorescent intensity and cell count, as obtained by flow cytometric analysis of cells post-culture for a test (Example 1) in which a sample 1 having FAM and the amino acid sequence given by SEQ ID NO: 4 was added to a HeLa cell culture medium, a test (Example 2) in which a sample 2 having FAM and the amino acid sequence given by SEQ ID NO: 2 was added to a HeLa cell culture medium, and a test (Example 3) in which FAM was added to a HeLa cell culture medium. The x-axis (horizontal axis) gives the fluorescent intensity and the y-axis (vertical axis) gives the cell count.

The results obtained in Examples 1 to 3 are given in FIG. 1 and Table 3. FIG. 1 provides a histogram of the cell count (vertical axis) and fluorescent intensity (horizontal axis) measured using the FL2 fluorescence detector of the indicated flow cytometer. Table 3 gives the MFI value provided by this measurement for each example.

TABLE 3

|  | Example 1 | Example 2 | Example 3 |
|---|---|---|---|
| MFI | 690 | 10.5 | 5.9 |

As shown in FIG. 1, for Example 1, which concerned the addition of a foreign substance introduction construct (sample 1) provided with peptide 1 and a fluorescent dye (FAM), and Example 2, which concerned the addition of a foreign substance introduction construct (sample 2) provided with peptide 2 and a fluorescent due (FAM), it was found that, based on the histogram shifting to the right on the horizontal axis, the fluorescent dye (FAM) functioning as the foreign substance was more efficiently introduced into the cytoplasm of the HeLa cells by peptide 1 and peptide 2 than in Example 3, in which only FAM was added. Comparing Example 1 and Example 2, the histogram for Example 1 underwent a more significant shift to the right on the horizontal axis than did the histogram for Example 2. Thus, it was determined that, in comparison to the foreign substance introduction construct provided with peptide 2, the foreign substance introduction construct provided with peptide 1 had a higher cell membrane permeability and could introduce the foreign substance more efficiently from outside the cell into the cell interior. This efficiency (cell membrane permeability), when compared using the MFI given in Table 3, was approximately 65.7-times higher for Example 1 than for Example 2.

While the detailed data are not provided, investigations by the present inventors have determined that not only in the case of the fluorescent dye, but also for the use of polypeptides, nucleic acids, and drugs as the foreign substance, such foreign substances are efficiently introduced from the cell exterior into the cytoplasm.

As is made clear in the preceding, in accordance with the herein disclosed art a foreign substance of interest can be efficiently introduced from outside a eukaryotic cell into at least the cytoplasm of the cell, through the use as a carrier peptide fragment of a peptide fragment that is provided with a repeat sequence in which the amino acid sequence with SEQ ID NO: 1 is repeated at least two or more times.

While specific examples of the herein disclosed art have been described in detail above, these are only illustrations and are not limitations on the claims. The art described in the claims encompasses various modifications and alterations of the specific examples provided above as illustrations.

The herein disclosed art provides an artificially constructed peptide fragment for introducing a foreign substance of interest from the outside of a eukaryotic cell (particularly cell wall-free cells from various animals as represented by humans and other mammals) into at least the cytoplasm of the cell. The herein disclosed art also provides a construct that is provided with this peptide fragment. Through the use of this construct, Through the use of this construct, a foreign substance of interest can be introduced effectively into target cells to obtain cells having the introduced foreign substance and an organ or biological tissue containing the cells having the foreign substance. In addition, therapeutic agents against diseases can be provided through the use of this construct.

Sequence Listing Free Text

SEQ ID NOs: 1 to 4 synthetic peptides

What is claimed is:

1. A peptide fragment comprising a repeat sequence in which the following amino acid sequence:

VVRSLVK (SEQ ID NO: 1)

is repeated at least two or more times.

2. The peptide fragment according to claim 1, wherein the boundary region between amino acid sequences given by SEQ ID NO: 1 in the repeat sequence either does not contain an additional amino acid residue or contains from 1 to 3 additional amino acid residues.

3. The peptide fragment according to claim 1, wherein the repeat sequence is provided with two of the amino acid sequences given by SEQ ID NO: 1.

4. A construct comprising the peptide fragment according to claim 1; and a foreign substance of interest bonded to the N-terminal side and/or the C-terminal side of the peptide fragment; wherein the foreign substance consists of one or more organic compounds selected from the group consisting of polypeptides, nucleic acids, dyes, and drugs.

5. A method for introducing a foreign substance of interest from outside a eukaryotic cell into at least the cytoplasm of the cell in vitro, the method comprising:

(1) a step of preparing the construct according to claim 4;

(2) a step of supplying the construct to a sample that contains the eukaryotic cells of interest; and (3) a step of incubating the sample to which the construct has been supplied, in order to introduce the construct into the eukaryotic cells in the sample.

6. The method according to claim 5, wherein the eukaryotic cells that are the target for the introduction of the construct are human or nonhuman mammalian cells.

* * * * *

SEQUENCE LISTING

```
<160> NUMBER OF SEQ ID NOS: 4

<210> SEQ ID NO 1
<211> LENGTH: 7
<212> TYPE: PRT
<213> ORGANISM: Artificial Sequence
<220> FEATURE:
<223> OTHER INFORMATION: synthetic peptide

<400> SEQUENCE: 1

Val Val Arg Ser Leu Val Lys
1               5

<210> SEQ ID NO 2
<211> LENGTH: 13
<212> TYPE: PRT
<213> ORGANISM: Artificial Sequence
<220> FEATURE:
<223> OTHER INFORMATION: synthetic peptide

<400> SEQUENCE: 2

Lys Lys Arg Thr Leu Arg Lys Asn Asp Arg Lys Lys Arg
1               5                   10

<210> SEQ ID NO 3
<211> LENGTH: 15
<212> TYPE: PRT
<213> ORGANISM: Artificial Sequence
<220> FEATURE:
<223> OTHER INFORMATION: synthetic peptide

<400> SEQUENCE: 3

Thr Leu Lys Glu Arg Cys Leu Gln Val Val Arg Ser Leu Val Lys
1               5                   10                  15

<210> SEQ ID NO 4
<211> LENGTH: 14
<212> TYPE: PRT
<213> ORGANISM: Artificial Sequence
<220> FEATURE:
```

-continued

```
<223> OTHER INFORMATION: synthetic peptide

<400> SEQUENCE: 4

Val Val Arg Ser Leu Val Lys Val Val Arg Ser Leu Val Lys
1               5                   10
```